United States Patent
Davison et al.

(10) Patent No.: US 11,553,939 B2
(45) Date of Patent: Jan. 17, 2023

(54) SURGICAL INSTRUMENTS WITH A RETENTION FEATURE THAT RETAINS A CUTTING ELEMENT

(71) Applicant: Ethicon LLC, Guaynabo, PR (US)

(72) Inventors: Mark Allen Davison, Maineville, OH (US); Benjamin D. Dickerson, Cincinnati, OH (US); Rudolph Henry Nobis, Mason, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 1092 days.

(21) Appl. No.: 16/176,575

(22) Filed: Oct. 31, 2018

(65) Prior Publication Data

US 2020/0129198 A1    Apr. 30, 2020

(51) Int. Cl.
*A61B 17/29*    (2006.01)
*A61B 17/295*    (2006.01)
*A61B 34/30*    (2016.01)
(Continued)

(52) U.S. Cl.
CPC ........ *A61B 17/295* (2013.01); *A61B 17/2909* (2013.01); *A61B 17/34* (2013.01); *A61B 34/30* (2016.02); *A61B 17/068* (2013.01); *A61B 2017/00017* (2013.01); *A61B 2017/00398* (2013.01); *A61B 2017/00473* (2013.01);
(Continued)

(58) Field of Classification Search
CPC .............. A61B 17/068; A61B 17/2909; A61B 17/295; A61B 17/34; A61B 18/12; A61B 18/1445; A61B 2017/00017; A61B 2017/00398; A61B 2017/00473; A61B 2017/00477; A61B 2017/2927; A61B 2017/2936; A61B 2018/00601;
(Continued)

(56) References Cited

U.S. PATENT DOCUMENTS

| | | | |
|---|---|---|---|
| 5,800,449 A * | 9/1998 | Wales | A61B 18/1447 606/205 |
| 7,150,097 B2 * | 12/2006 | Sremcich | A61B 18/1445 29/857 |
| 8,333,780 B1 | 12/2012 | Pedros et al. | |
| 8,968,309 B2 * | 3/2015 | Roy | A61B 18/1445 606/205 |
| 2004/0193146 A1 | 9/2004 | Lee | |
| 2005/0096651 A1 * | 5/2005 | Truckai | A61B 18/1442 606/51 |

(Continued)

FOREIGN PATENT DOCUMENTS

| | | |
|---|---|---|
| EP | 2489318 A1 | 8/2012 |
| EP | 3321047 A1 | 5/2018 |
| WO | 2016186999 A1 | 11/2016 |

OTHER PUBLICATIONS

ISR-WO from PCT/IB2019/059269, which claims priority to the present application, dated Feb. 11, 2020.

*Primary Examiner* — Michael F Peffley
(74) *Attorney, Agent, or Firm* — Vorys, Sater, Seymour and Pease LLP

(57) ABSTRACT

An end effector includes first and second jaws movable between open and closed positions, a guide track defined in the second jaw, and a cutting element extendable into the guide track and longitudinally movable within the guide track. A retention feature is positioned within the guide track and operatively couples the cutting element to a drive rod. The drive rod is actuatable to move the cutting element within the guide track, and the retention feature is larger than a width of an opening to the guide track such that the retention feature is retained within the guide track as the cutting element moves.

18 Claims, 9 Drawing Sheets

(51) Int. Cl.
  *A61B 17/34* (2006.01)
  *A61B 17/068* (2006.01)
  *A61B 17/00* (2006.01)

(52) U.S. Cl.
  CPC ............... *A61B 2017/00477* (2013.01); *A61B 2017/2927* (2013.01); *A61B 2017/2936* (2013.01)

(58) Field of Classification Search
  CPC .... A61B 2018/1452; A61B 2018/1455; A61B 34/30; A61B 34/71
  USPC .......................................................... 606/51
  See application file for complete search history.

(56) References Cited

U.S. PATENT DOCUMENTS

| | | | |
|---|---|---|---|
| 2010/0274244 A1* | 10/2010 | Heard ................ | A61B 18/1442 606/45 |
| 2011/0054472 A1* | 3/2011 | Romero ............. | A61B 18/1445 606/51 |
| 2011/0087221 A1* | 4/2011 | Siebrecht ............ | A61B 17/295 606/45 |
| 2014/0107667 A1 | 4/2014 | Komuro et al. | |
| 2014/0236149 A1* | 8/2014 | Kharin ............... | A61B 18/1445 606/45 |
| 2015/0305804 A1* | 10/2015 | Parihar ................. | A61B 17/29 606/51 |
| 2017/0095922 A1 | 4/2017 | Licht et al. | |
| 2017/0252096 A1 | 9/2017 | Felder et al. | |
| 2018/0206904 A1 | 7/2018 | Felder et al. | |
| 2018/0311471 A1 | 11/2018 | Kampa et al. | |

\* cited by examiner

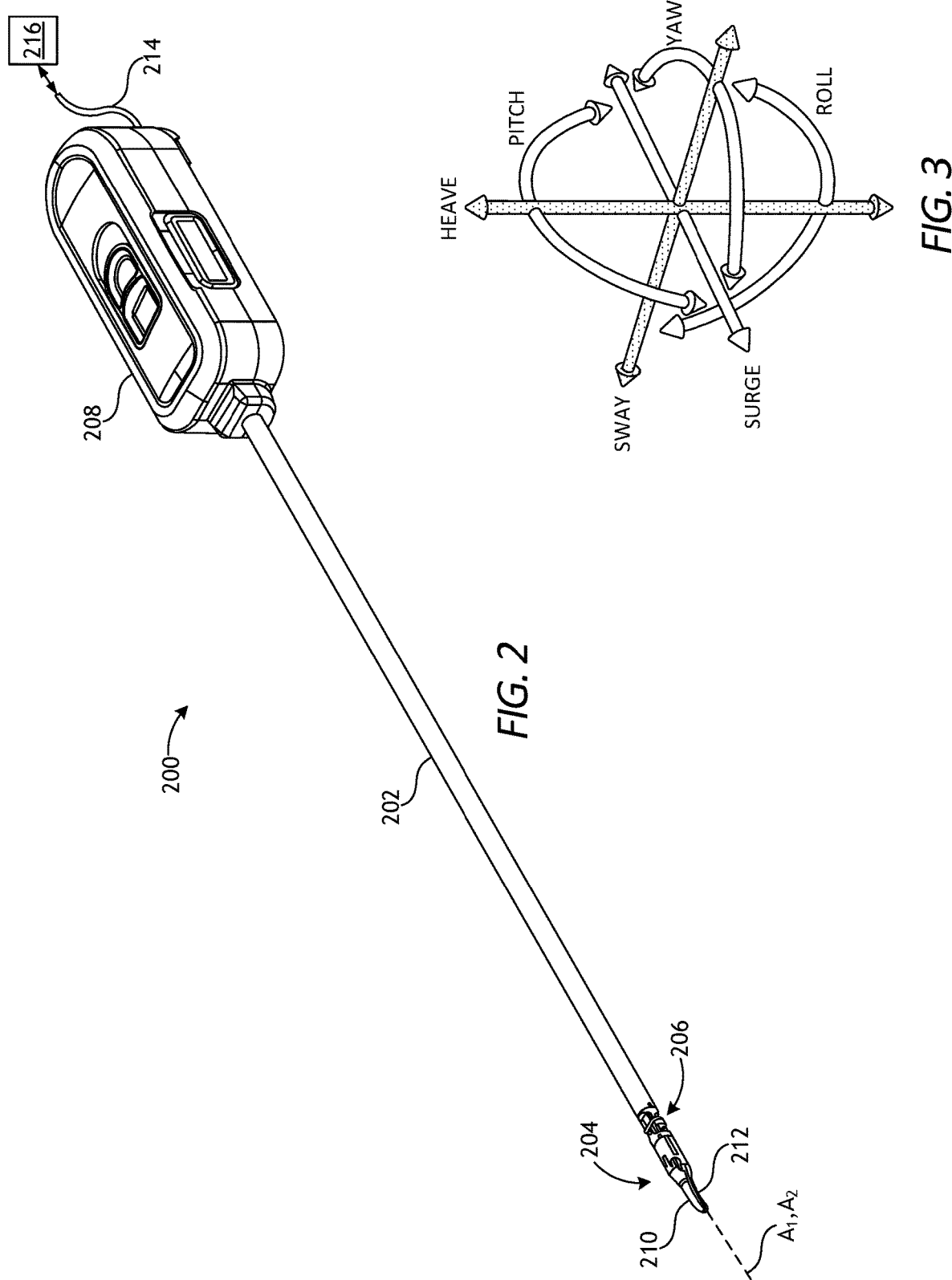

SURGICAL INSTRUMENTS WITH A RETENTION FEATURE THAT RETAINS A CUTTING ELEMENT

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

One type of end effector is a tissue grasper that has opposing jaws capable of closing down and "grasping" onto tissue, and some tissue graspers incorporate a knife that can be advanced distally to transect grasped tissue. The knife typically traverses a knife slot (alternately referred to as a "guide track") provided in one or both of the jaws as it moves distally, and the knife slot helps maintain the knife in a predetermined path (straight, curved, etc.). After cutting the tissue, the knife is retracted proximally to a home position so that it is not exposed when the jaws are open. One issue applicable to many tissue graspers with integral knives is that the thickness of the grasped tissue influences the degree to which the jaws can close. If the jaws are unable to close sufficiently, the knife may be able escape from the knife slot during movement and cutting. This can result in the knife jamming the mechanism upon retraction and/or inadvertently cutting tissue outside the target location.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2 is an isometric side view of an example surgical tool that may incorporate some or all of the principles of the present disclosure.

FIG. 3 illustrates potential degrees of freedom in which the wrist of the surgical tool of FIG. 2 may be able to articulate (pivot) and translate.

DETAILED DESCRIPTION

The present disclosure is related to robotic surgical systems and, more particularly, to tissue grasper end effectors with an integral cutting element designed to be retained in a guide track during tissue transection.

One example end effector includes first and second jaws movable between open and closed positions, and a guide track may be defined in the second jaw. A cutting element may be extendable into the guide track and longitudinally movable within the guide track. A retention feature may be positioned within the guide track to operatively couple the cutting element to a drive rod, and the drive rod may be actuatable to move the cutting element within the guide track. As described herein an opening to the guide track may be smaller than the retention feature such that the retention feature and the cutting element may be retained within the guide track as the cutting element moves during operation. In some embodiments, the end effector may further include a longitudinal support structure defining a longitudinal channel that receives the drive rod. The drive rod may be slidable within the channel and the longitudinal support structure may help mitigate buckling of the drive rod.

Figure 1:
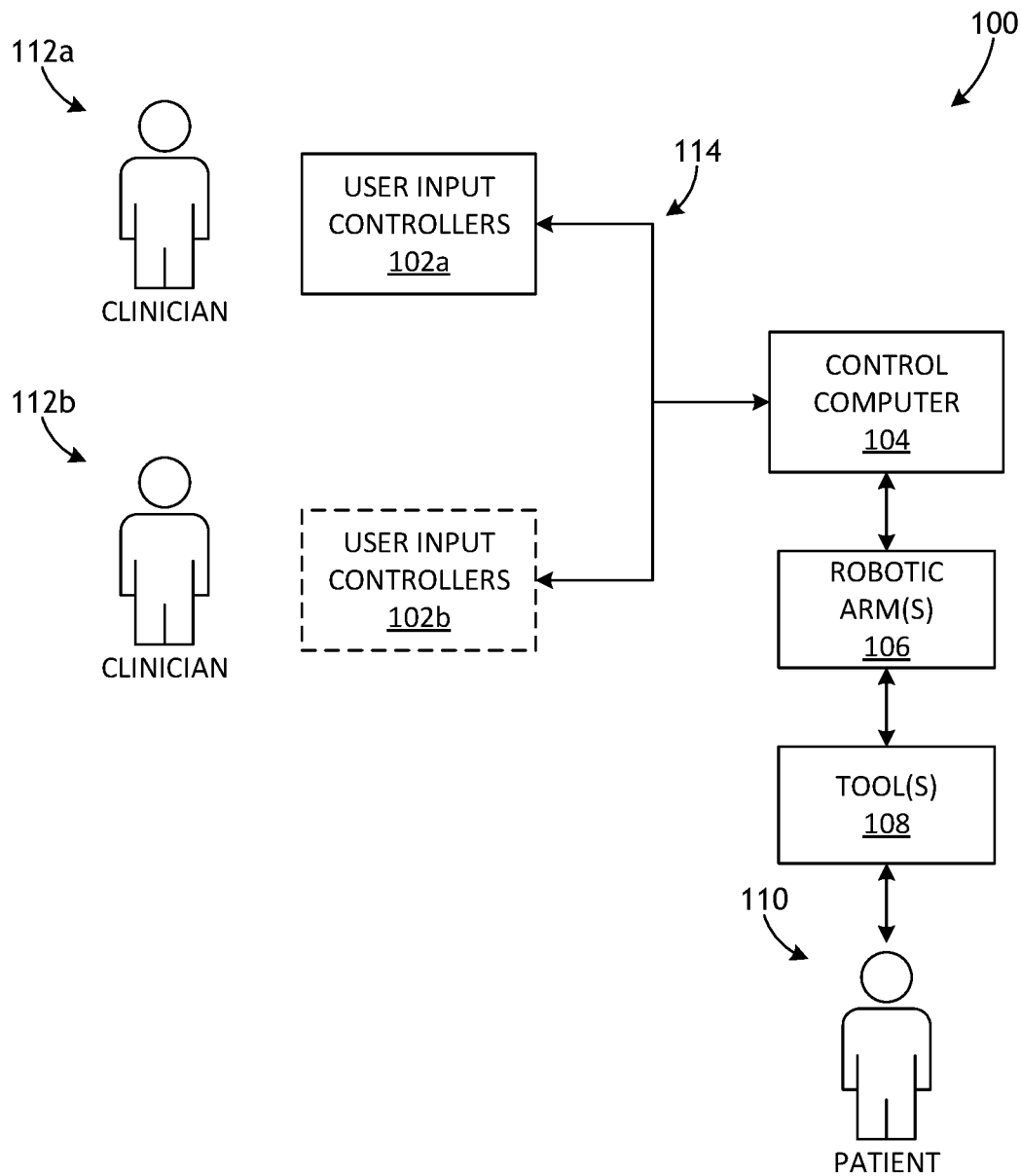
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112a,b via a display to provide a visual indication of various surgical instrument metrics, such as the amount of force being applied to the surgical instrument (i.e., a cutting instrument or dynamic clamping member).

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The surgical tool 200 can have any of a variety of configurations capable of performing at least one surgical function. For example, the surgical tool 200 may include, but is not limited to, forceps, a grasper, a needle driver, scissors, an electro cautery tool, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can have a variety of sizes, shapes, and configurations. In the illustrated embodiment, the end effector 204 comprises a tissue grasper and vessel sealer that include opposing jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot). The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 204) with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate movement and articulation of the end effector 204 relative to the shaft 202. Moving (actuating) at least some of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

Figure 4:
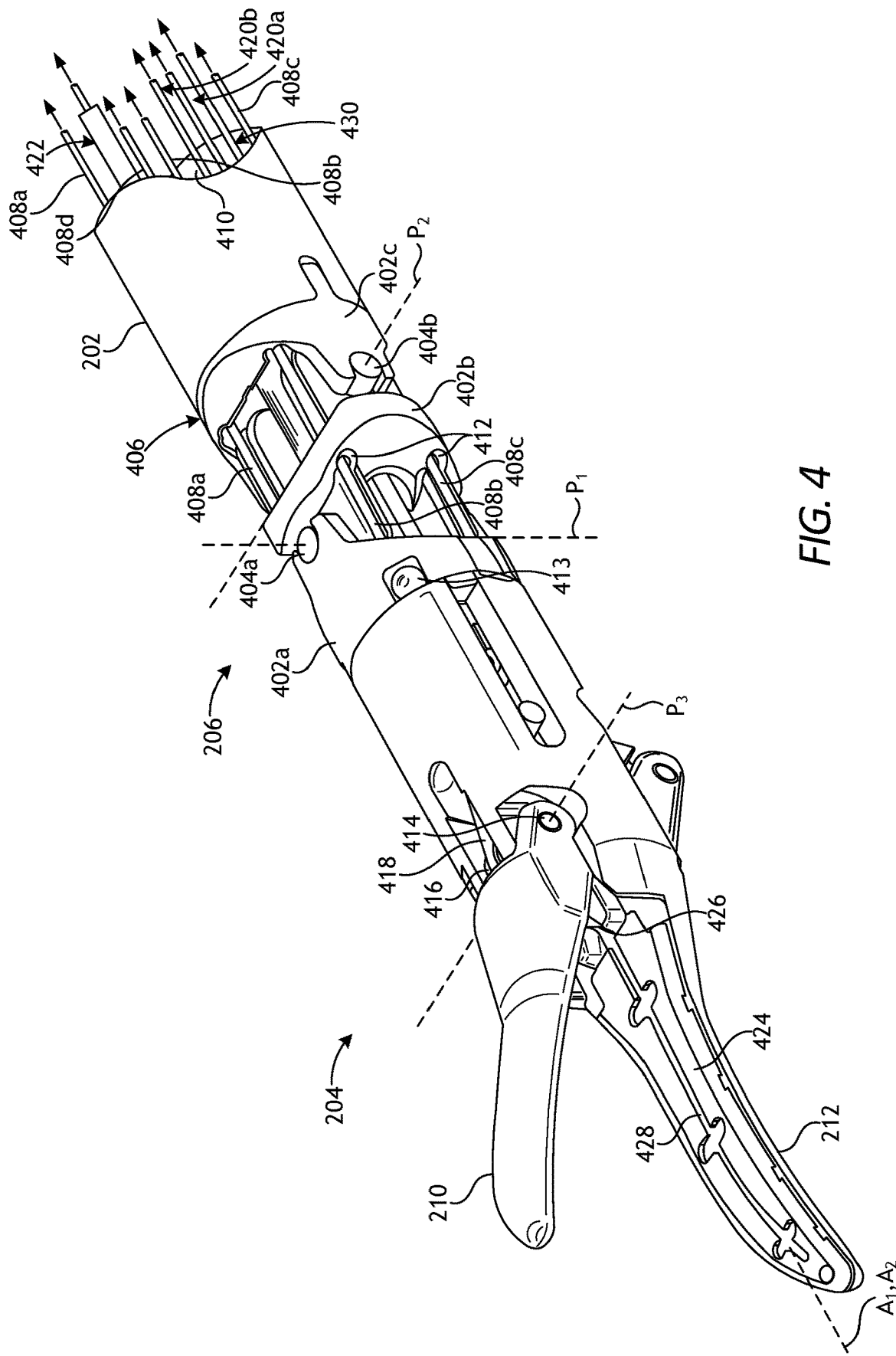
FIG. 4 is an enlarged isometric view of the distal end of the surgical tool of FIG. 2.

FIG. 4 is an enlarged isometric view of the distal end of the surgical tool 200 of FIG. 2. More specifically, FIG. 4 depicts an enlarged view of the end effector 204 and the wrist 206, with the jaws 210, 212 of the end effector 204 in the open position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" linkage 402a, a second or "intermediate" linkage 402b, and a third or "proximal" linkage 402c. The linkages 402a-c are configured to facilitate articulation of the end effector 204 relative to the elongate shaft 202, e.g., angle the end effector 204 relative to the longitudinal axis $A_1$ of the shaft 202. In the Illustrated embodiment, articulation via the linkages 402a-c may be limited to pitch only, yaw only, or a combination thereof. As illustrated, the distal end of the distal linkage 402a may be coupled to the end effector 204 and, more particularly, to the lower jaw 212 (or an extension of the lower jaw 212). The proximal end of the distal linkage 402a may be rotatably coupled to the intermediate linkage 402b at a first axle 404a, and the intermediate linkage 402b may also be rotatably coupled to the proximal linkage 402c at a second axle 404b. The proximal end of the proximal linkage 402c may be coupled to a distal end 406 of the shaft 202 (or alternatively a shaft adapter).

The wrist 206 provides a first pivot axis $P_1$ that extends through the first axle 404a and a second pivot axis $P_2$ that extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis P$_2$ provides "pitch" articulation of the end effector 204. Alternatively, the first pivot axis P$_1$ could be configured to provide "pitch" articulation and the second pivot axis P$_2$ could be configured to provide "yaw" articulation.

A plurality of drive cables, shown as drive cables 408a, 408b, 408c, and 408d, extend longitudinally within a lumen 410 defined by the shaft 202 (and/or a shaft adaptor) and pass through the wrist 206 to be operatively coupled to the end effector 204. The lumen 410 can be a single lumen, as illustrated, or can alternatively comprise a plurality of independent lumens, where each lumen receives one or more of the drive cables 408a-d.

The drive cables 408a-d form part of the cable driven motion system briefly described above, and may be referred to and otherwise characterized as cables, bands, lines, cords, wires, woven wires, ropes, strings, twisted strings, elongate members, etc. The drive cables 408a-d can be made from a variety of materials including, but not limited to, metal (e.g., tungsten, stainless steel, etc.) a polymer (e.g., ultra-high molecular weight polyethylene), a synthetic fiber (e.g., KEVLAR®, VECTRAN®, etc.), or any combination thereof. While four drive cables 408a-d are depicted in FIG. 4, more or less than four drive cables 408a-d may be included, without departing from the scope of the disclosure.

The drive cables 408a-d extend proximally from the end effector 204 to the drive housing 208 (FIG. 2) where they are operatively coupled to various actuation mechanisms (e.g., capstans) or devices housed therein to facilitate longitudinal movement (translation) of the drive cables 408a-d within the lumen 410. Selective actuation of all or a portion of the drive cables 408a-d causes the end effector 204 to articulate (pivot) relative to the shaft 202. More specifically, selective actuation causes a corresponding drive cable 408a-d to translate longitudinally within the lumen 410 and thereby cause pivoting movement of the end effector 204. Moving the drive cables 408a-d can be accomplished in a variety of ways, such as by triggering an associated actuator or mechanism (e.g., a capstan) operatively coupled to or housed within the drive housing 208 (FIG. 2). Moving a given drive cable 408a-d constitutes applying tension (i.e., pull force) to the given drive cable 408a-d in a proximal direction, which causes the given drive cable 408a-d to translate and thereby cause the end effector 204 to move (articulate) relative to the shaft 202. As will be appreciated, applying tension to and moving one drive cable 408a-d may result in the slackening of a drive cable 402a-d angularly (or diagonally) opposite to the moving drive cable 402a-d.

The drive cables 408a-d each extend longitudinally through the first, second, and third linkages 402a-c. In some embodiments, each linkage 402a-c may define four, equidistantly-spaced apertures 412 (only two labeled) configured to guide the drive cables 408a-d through the wrist 206. The apertures 412 of each linkage 402a-c may coaxially align when the end effector 204 is in the unarticulated position. The apertures 412 may provide rounded edges and sufficiently large radii to help reduce friction between the drive cables 408a-d and the linkages 402a-c and/or help prevent the drive cables 408a-d from twisting or moving radially inward or outward during articulation.

In some embodiments, the distal end of each drive cable 408a-d may terminate at the first linkage 402a, thus operatively coupling each drive cable 408a-d to the end effector 204 and, more particularly, to the lower jaw 212. The distal end of each drive cable 408a-d may be enlarged to facilitate fixed attachment thereof to the end effector 204. In some embodiments, as illustrated, the distal end of each drive cable 408a-d may include a ball crimp 413 (only one shown). In other embodiments, however, the distal end of each drive cable 408a-d may include a weld, an adhesive attachment, a press fit, or any combination of the foregoing.

The jaws 210, 212 may be moved between the closed and open positions by pivoting the upper jaw 210 relative to the lower jaw 212. In the illustrated embodiment, the upper jaw 210 may be rotatably coupled (mounted) to the lower jaw 212 at a jaw axle 414. A third pivot axis P$_3$ extends through the jaw axle 414 and is generally perpendicular (orthogonal) to the first pivot axis P$_1$ and parallel to the second pivot axis P$_2$. In this embodiment, the lower jaw 212 remains stationary as the upper jaw 210 pivots about the third pivot axis P$_3$. In other embodiments, however, the jaws 210, 212 may be moved between the closed and open positions by moving (pivoting) both jaws 210, 212, without departing from the scope of the disclosure.

A central pulley 416 (partially visible) may be mounted to the jaw axle 414 and receive a jaw cable 418 that may be actuated to selectively open and close the jaws 210, 212. Similar to the drive cables 408a-d, the jaw cable 418 extends longitudinally within the lumen 410 and passes through the wrist 206. The jaw cable 418 may form part of the cable driven motion system described herein and, therefore, may extend proximally from the end effector 204 to the drive housing 208 (FIG. 2). The jaw cable 418 may comprise a single line or wire looped around the central pulley 416 and opposing first and second ends 420a and 420b of the jaw cable 418 extend proximally to the drive housing 208. The ends 420a,b of the jaw cable 418 may be operatively coupled to individual (discrete) actuation mechanisms (e.g., two capstans) housed within the drive housing 208. Actuation of corresponding drive inputs associated with each actuation mechanism will cooperatively cause tension or slack in the jaw cable 418 and thereby cause the upper jaw 210 to rotate about the third pivot axis P$_3$ between the open and closed positions.

In some embodiments, an electrical conductor 422 may supply electrical energy to the end effector 204 and, more particularly, to an electrode 424 included in the end effector 204. The electrical conductor 422 extends longitudinally within the lumen 410, through the wrist 206, and terminates at the electrode 424. In the illustrated embodiment, the electrode 424 is mounted to (e.g., overmolded onto) or otherwise forms part of the lower jaw 212. In other embodiments, however, the electrode 424 may form part of the upper jaw 210, or may alternatively be coupled to or form part of both jaws 210, 212, without departing from the scope of the disclosure. In some embodiments, the electrical conductor 422 and the power cable 214 (FIG. 2) may comprise the same structure. In other embodiments, however, the electrical conductor 422 may be electrically coupled to the power cable 214, such as at the drive housing 208 (FIG. 2). In yet other embodiments, the electrical conductor 422 may extend to the drive housing 208 where it is electrically coupled to an internal power source, such as batteries or fuel cells.

In some embodiments, the electrical conductor 422 may comprise a wire. In other embodiments, however, the electrical conductor 422 may comprise a rigid or semi-rigid shaft, rod, or strip (ribbon) made of a conductive material. The electrical conductor 422 may be partially covered with an insulative covering (overmold) made of a non-conductive material. The insulative covering, for example, may comprise a plastic applied to the electrical conductor 422 via heat shrinking, but could alternatively be any other non-conductive material.

The end effector 204 may be configured for monopolar or bipolar operation. In at least one embodiment, the electrical energy conducted through the electrical conductor 422 may comprise radio frequency ("RF") energy exhibiting a frequency between about 100 kHz and 1 MHz. In a process known as Joule heating (resistive or Ohmic heating) the RF energy is transformed into heat within the target tissue due the tissue's intrinsic electrical impedance, thereby increasing the temperature of target tissue. Accordingly, heating of the target tissue is used to achieve various tissue effects such as cauterization and/or coagulation and thus may be particularly useful for sealing blood vessels or diffusing bleeding during a surgical procedure.

In the illustrated embodiment, the end effector 204 comprises a combination tissue grasper and vessel sealer that includes a cutting element 426 (mostly hidden behind other structures), alternately referred to as a "knife" or "blade." The cutting element 426 is aligned with and configured to traverse a guide track 428 (alternately referred to as a "defined" or "structured" pathway) defined longitudinally in one or both of the jaws 210, 212. The cutting element 426 may be operatively coupled to a drive rod 430 (alternately referred to as "knife rod," "actuation rod," or "cutting rod") that extends longitudinally within the lumen 410 and passes through the wrist 206. Longitudinal movement (translation) of the drive rod 430 correspondingly moves the cutting element 426 within the guide track(s) 428 in the same direction.

The drive rod 430 may comprise a rigid or semi rigid elongate member, such as a rod or shaft (e.g., a hypotube, a hollow rod, a solid rod, etc.), a wire, a ribbon, a push cable, or any combination thereof. The drive rod 430 can be made from a variety of materials including, but not limited to, metal (e.g., tungsten, nitinol, stainless steel, etc.), a polymer, or a composite material. The drive rod 430 may have a circular cross-section, but may alternatively exhibit a polygonal cross-section without departing from the scope of the disclosure.

Similar to the drive and jaw cables 408a-d, 418, the drive rod 430 may form part of the cable driven motion system and, therefore, may extend proximally from the cutting element 426 to the drive housing 208 (FIG. 2). The proximal end of the drive rod 430 may be operatively coupled to an actuation mechanism or device housed within the drive housing 208. Selective actuation of the corresponding drive input associated with the actuation mechanism or device will cause the drive rod 430 to move distally or proximally within the lumen 410, and correspondingly move the cutting element 426 in the same direction.

In example operation of the end effector 204, the jaws 210, 212 may be actuated to close and grasp onto tissue, following which the electrode 424 may be supplied with electrical energy, which is transformed into heat within the grasped tissue to cauterize, coagulate, and/or otherwise seal the tissue. The cutting element 426 may then be advanced distally along the guide track(s) 428 to cut (transect) the grasped and sealed tissue. Alternatively, the cutting element 426 may be advanced prior to the application of electrical energy to cut unsealed tissue to facilitate dissection of non-vascular tissue. According to embodiments of the disclosure, and as described in more detail below, the drive rod 430 that pushes the cutting element distally may be supported against buckling within the end effector 204 with a longitudinal support structure (not visible).

Figure 5:
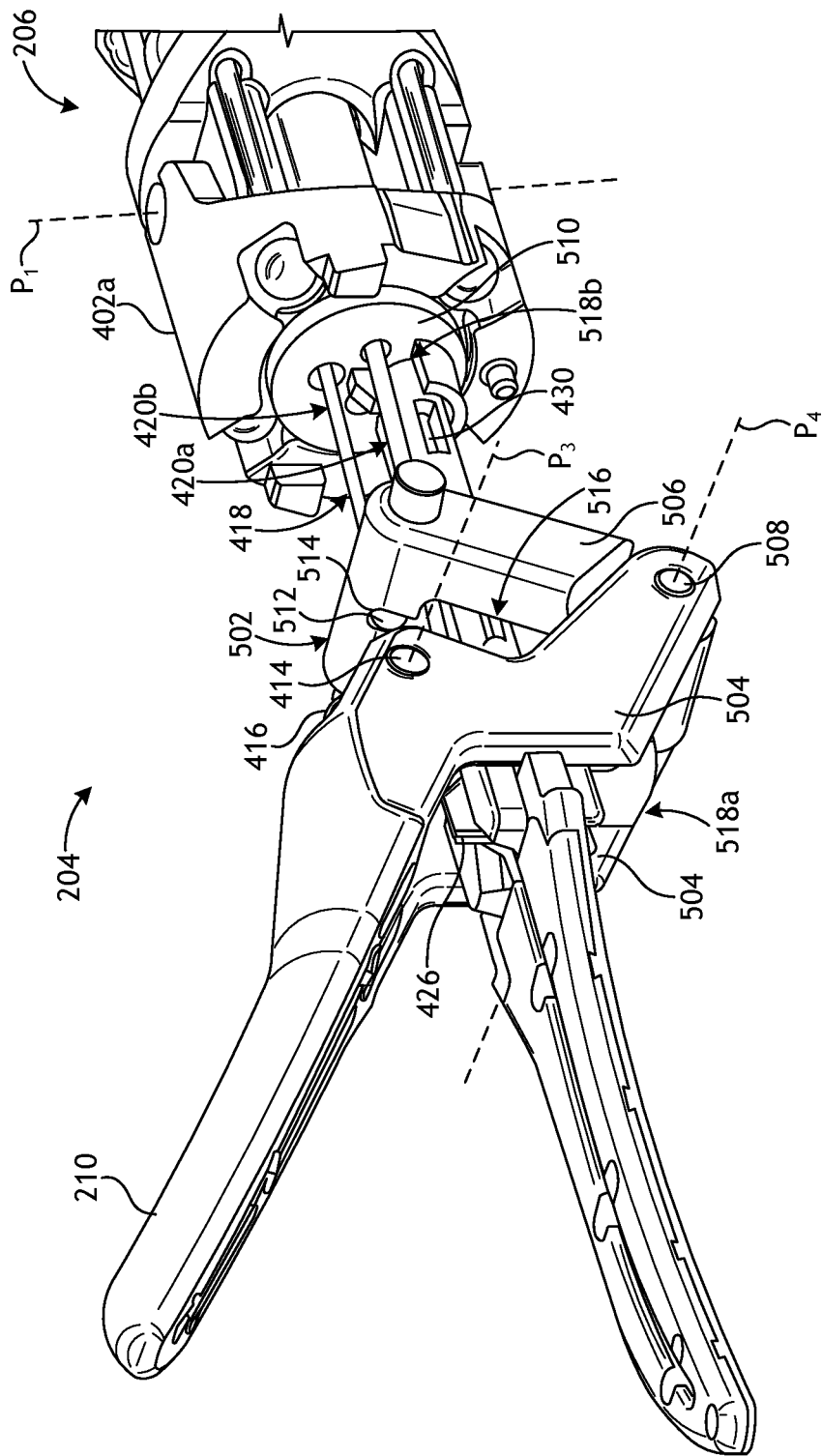
FIG. 5 is an isometric side view of the end effector of FIG. 4 in an open position, according to one or more embodiments.

FIG. 5 is an isometric side view of the end effector 204 in an open position, according to one or more embodiments. More particularly, FIG. 5 depicts the upper jaw 210 pivoted to the open position, and the lower jaw 212 (FIG. 4) is omitted to enable viewing of the internal components of the end effector 204. As illustrated, the end effector 204 includes a pivot link 502 operatively coupled to the upper jaw 210. More specifically, the upper jaw 210 provides or otherwise defines one or more legs 504 that are pivotably coupled to a corresponding one or more legs 506 (one shown, one occluded) of the pivot link 502 at a pivot axle 508. A fourth pivot axis $P_4$ extends through the pivot axle 508 and may be generally perpendicular (orthogonal) to the first pivot axis $P_1$ and parallel to the third pivot axis $P_3$.

The central pulley 416 (mostly hidden from view) is rotatably supported on the jaw axle 414, and the jaw cable 418 loops around the central pulley 416 and includes opposing ends 420a,b that extend proximally through the wrist 206. In the illustrated embodiment, the ends 420a,b of the jaw cable 418 extend through a distal adapter 510 operatively coupled to the wrist 206 and, more particularly, to the distal linkage 402a. In other embodiments, however, the distal adapter 510 may be omitted.

The jaw cable 418 may be operatively coupled to the pivot link 502 such that movement (i.e., longitudinal translation) of the jaw cable 418 correspondingly moves the pivot link 502. For example, a cable anchor 512 may be secured to or otherwise form part of one proximally extending end 420a,b of the jaw cable 418 and may help operatively couple the jaw cable 418 to the pivot link 502. In the illustrated embodiment, the cable anchor 512 comprises a ball crimp receivable within a socket 514 defined by the pivot link 502. In other embodiments, however, the cable anchor 512 may alternatively include, but is not limited to, a weld, an adhesive attachment, a press fit engagement, or any combination of the foregoing and capable of being removably or permanently attached to the pivot link 502.

To move the jaws 210, 212 to the open position, the jaw cable 418 may be actuated to move the pivot link 502 distally. As the pivot link 502 moves distally, the legs 506 of the pivot link 502 act on the legs 504 of the upper jaw 210 at the pivot axle 508. More specifically, distal movement of the pivot link 502 forces the legs 504 downward in rotation about the fourth pivot axis $P_4$, and downward movement of the legs 504 correspondingly causes the upper jaw 210 to pivot about the third pivot axis $P_3$, similar to the operation of a two-bar linkage. As it pivots about the third pivot axis $P_3$, the upper jaw 210 is moved to the open position. To move the upper jaw 210 back to the closed position, the jaw cable 418 may be actuated to move the pivot link 502 proximally, which causes the pivot link 502 to pull upward on the legs 504 of the upper jaw 210 in rotation about the fourth pivot axis $P_4$. Upward movement of the legs 504 correspondingly causes the upper jaw 210 to pivot about the third pivot axis $P_3$ and moves the upper jaw 210 back to the closed position.

In the illustrated embodiment, the end effector 204 may further include a longitudinal support structure 516 (partially hidden) configured to support the drive rod 430 against buckling. More specifically, as the cutting element 426 is advanced distally within the guide track(s) 428 to transect tissue grasped by the closed jaws 210, 212, the tissue will generate an opposing force (loading) in the proximal direction that resists distal movement of the cutting element 426. If the resistance load of the tissue surpasses the compressive capacity of the drive rod 430 in the distal direction, the drive rod 430 may buckle and the cutting operation will be compromised. The longitudinal support structure 516 may be configured to enhance or supplement the compressive capacity of the drive rod 430 and thereby mitigate buckling.

As illustrated in FIG. 5, the longitudinal support structure 516 includes a first or "distal" end 518a and a second or "proximal" end 518b opposite the distal end 518a. In some embodiments, the distal end 518a may be coupled to or otherwise supported by the lower jaw 212 (FIG. 4), and the proximal end 518b may extend toward the wrist 206. In at least one embodiment, the proximal end 518b may be supported by the distal adapter 510. In other embodiments, however, the proximal end 518b may penetrate and otherwise extend within the distal adapter 510. In yet other embodiments, the distal adapter 510 may be omitted and the proximal end 518b may be coupled to or otherwise supported by the distal linkage 402a.

The longitudinal support structure 516 may prove advantageous in allowing for full protection from buckling under a push load provided by the drive rod 430. Moreover, by receiving the drive rod 430 within the longitudinal support structure 516, additional space is opened up in the distal end of the end effector 204. This additional space allows for more beneficial packaging and locating of the drive cables 408a-d (FIG. 4). Furthermore, the additional space may also allow the drive rod 430 to be made larger or of a noncircular cross-section, which may increase the compressive strength of the drive rod 430 and potentially enable cheaper manufacturing processes.

Figure 6A:
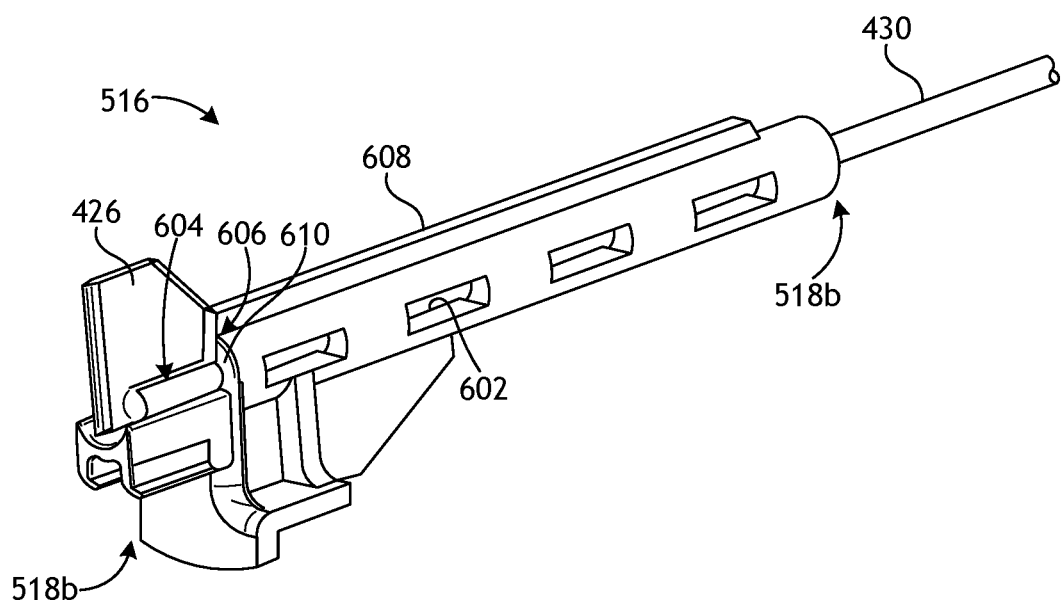
FIGS. 6A and 6B are enlarged isometric views of the longitudinal support structure of FIG. 5, according to one or more embodiments.
Figure 6B:
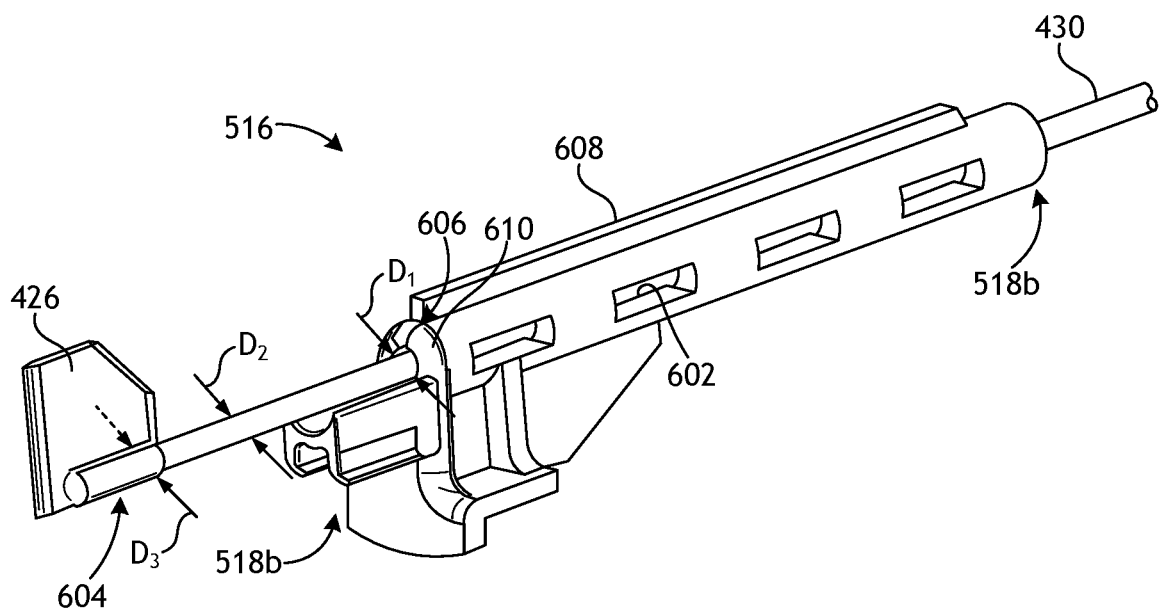

FIGS. 6A and 6B are enlarged isometric views of the longitudinal support structure 516, according to one or more embodiments. More specifically, FIG. 6A depicts the cutting element 426 in a proximal or "home" position relative to the longitudinal support structure 516, and FIG. 6B depicts the cutting element 426 in a distal or "extended" position as moved by the drive rod 430.

The longitudinal support structure 516 may provide or otherwise define a longitudinal channel 602 that extends at least partially between the distal and proximal ends 518a,b. The channel 602 may be sized and otherwise configured to slidably receive the drive rod 430. As best seen in FIG. 6B, the channel 602 may exhibit a first or "inner" diameter $D_1$ that is larger than a second or "outer" diameter $D_2$ of the drive rod 430. The inner diameter $D_1$ may be large enough to allow the drive rod 430 to reciprocate within the channel 602, but small enough to prevent the drive rod 430 from buckling when the cutting element 426 assumes resistance loading in the proximal direction during operation.

The cutting element 426 may be attached to the distal end of the drive rod 430 at an interactively coupled retention feature 604. The retention feature 604 may comprise any attachment or coupling means that removably or permanently fixes the cutting element 426 to the drive rod 430. For example, the retention feature 604 may comprise, but is not limited to, a welded interface, an adhesive attachment, an interference or shrink fit, an overmold (e.g., a shaped block of material or a support block), one or more mechanical fasteners, or any combination thereof. In at least one embodiment, the retention feature 604 may comprise a formed shape on the drive rod 430 or alternatively on the cutting element 426. As described herein, the retention feature 604 may also help prevent the cutting element 426 from exiting or disengaging the guide track 428 (FIG. 4) defined in the lower jaw 212 (FIG. 4).

In some embodiments, the longitudinal support structure 516 may also provide or otherwise define a hard stop 606 at or near the distal end 518a. In the illustrated embodiment, the hard stop 606 may comprise a longitudinal rib 608 positioned to align with the cutting element 426 when the cutting element 426 is in the home position (FIG. 6A). When the drive rod 430 moves the cutting element 426 proximally toward the home position, the cutting element 426 may eventually contact the longitudinal rib 608, which stops its proximal travel.

As will be appreciated, the hard stop 606 is not limited to the longitudinal rib 608 but is depicted merely for example. Indeed, any structure or device included on the longitudinal support structure 516 may serve as the hard stop 606 to stop proximal travel of the cutting element 426 and provide a homing location. In other embodiments, for example, or in addition to the longitudinal rib 608, a distal opening 610 to the channel 602 may form part of the hard stop 606. More specifically, the retention feature 604 may exhibit a third diameter $D_3$ (FIG. 6B) or otherwise a cross-sectional size that is larger than the inner diameter $D_1$ of the channel 602 at the distal opening 610. Consequently, when the drive rod 430 moves the cutting element 426 to the home position, the retention feature 604 will be stopped at the outer wall(s) of the distal opening 610, which stops further proximal movement of the cutting element 426.

Figure 7:
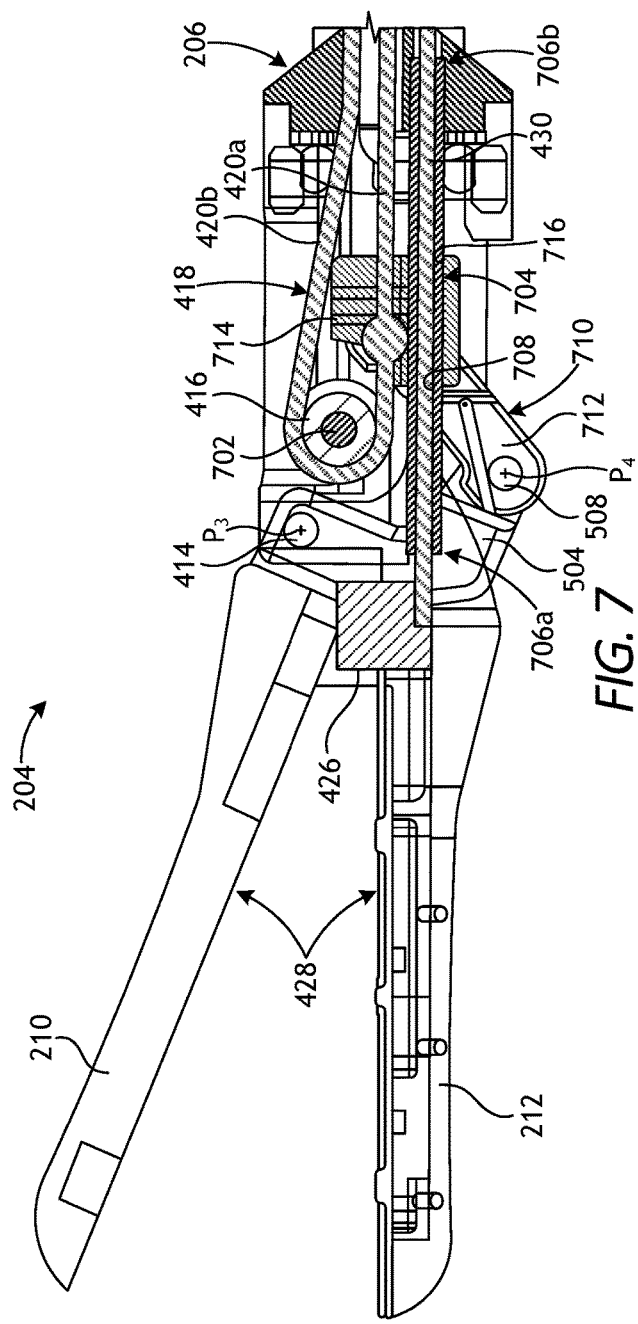
FIG. 7 is a partial cross-sectional side view of an alternative embodiment of the end effector of FIG. 4, according to one or more additional embodiments.

FIG. 7 is a partial cross-sectional side view of an alternative embodiment of the end effector 204, according to one or more additional embodiments. In the depicted view, the jaws 210, 212 are in the open position, and the lower jaw 212 is shown in phantom (transparent) to enable viewing of the internal components of the end effector 204. In the illustrated embodiment, the central pulley 416 is rotatably supported on a pulley axle 702 that may be coupled to the lower jaw 212. The jaw cable 418 loops around the central pulley 416 and its opposing ends 420a,b extend proximally through the wrist 206.

The end effector 204 may further include a longitudinal support structure 704 similar in some respects to the longitudinal support structure 516 of FIGS. 5 and 6A-6B. Similar to the longitudinal support structure 516, for example, the longitudinal support structure 704 may be configured to support the drive rod 430 against buckling caused by resistance loading assumed on the cutting element 426 as it advances distally within the guide track(s) 428 to cut tissue. As illustrated, the longitudinal support structure 704 includes a first or "distal" end 706a and a second or "proximal" end 706b opposite the distal end 706a. In some embodiments, the distal end 706a may be coupled to or otherwise supported by the lower jaw 212, and the proximal end 706b may extend to the wrist 206. The proximal end 706b may be coupled to or otherwise supported by the wrist 206. In at least one embodiment, as illustrated, the proximal end 706b may penetrate the wrist 206 a short distance.

The longitudinal support structure 704 may provide a longitudinal channel 708 that extends between the distal and proximal ends 706a,b, and the channel 708 may be sized and otherwise configured to slidably receive the drive rod 430 such that the drive rod 430 is able to translate back and forth within the channel 708 with little or no resistance. The channel 708, however, may be small enough to prevent the drive rod 430 from buckling when the cutting element 426 assumes resistance loading in the proximal direction during operation.

The end effector 204 may further include a pivot link 710 similar in some respects to the pivot link 502 of FIG. 5. Similar to the pivot link 502, for example, the pivot link 710 may be operatively coupled to the upper jaw 210 and actuatable to pivot the upper jaw 210 about the jaw axle 414 between the open and closed positions. Moreover, the pivot link 710 may include one or more legs 712 pivotably coupled to the one or more legs 504 of the upper jaw 210 at the pivot axle 508.

Unlike the pivot link 502 of FIG. 5, however, the pivot link 710 may include a sliding element 714 driven by the jaw cable 418 to actuate the pivot link 710 and thereby move the upper jaw 210. More specifically, the sliding element 714 may define a sliding aperture 716 sized to receive the longitudinal support structure 704 such that the sliding element 714 is able to translate back and forth along the exterior of the longitudinal support structure 704 with little or no resistance. The jaw cable 418 may be operatively coupled to the pivot link 710 at or near the sliding element 714 such that movement (i.e., longitudinal translation) of the jaw cable 418 correspondingly moves the sliding element 714 (and the pivot link 710). As illustrated, the cable anchor 512 may operatively couple the jaw cable 418 to the sliding element 714.

To move the jaws 210, 212 to the open position, the jaw cable 418 may be actuated to move the pivot link 710 distally and, more specifically, slide the sliding element 714 along the exterior of the longitudinal support structure 704 in the distal direction. As the sliding element 714 moves distally, the leg(s) 712 of the pivot link 710 act on the leg(s) 504 of the upper jaw 210 at the pivot axle 508 and force the leg(s) 504 downward in rotation about the fourth pivot axis $P_4$, and downward movement of the leg(s) 504 correspondingly causes the upper jaw 210 to pivot about the third pivot axis $P_3$ to move the upper jaw 210 to the open position. To move the jaws 210, 212 back to the closed position, the jaw cable 418 may be actuated to slide the sliding element 714 along the exterior of the longitudinal support structure 704 in the proximal direction, which causes the pivot link 710 to pull upward on the legs 504 of the upper jaw 210 in rotation about the fourth pivot axis $P_4$. Upward movement of the legs 504 correspondingly causes the upper jaw 210 to pivot about the third pivot axis $P_3$ and move the upper jaw 210 back to the closed position.

Accordingly, the longitudinal support structure 704 shown in FIG. 7 may be multifunctional. The longitudinal support structure 704 may support the drive rod 430 against buckling caused by resistance loading assumed on the cutting element 426 as it advances distally within the guide track(s) 428 to cut tissue. However, the longitudinal support structure 704 may also serve as a guide rod for the closure system, including the pivot link 710, the sliding element 714, and the jaw cable 418.

Figure 8:
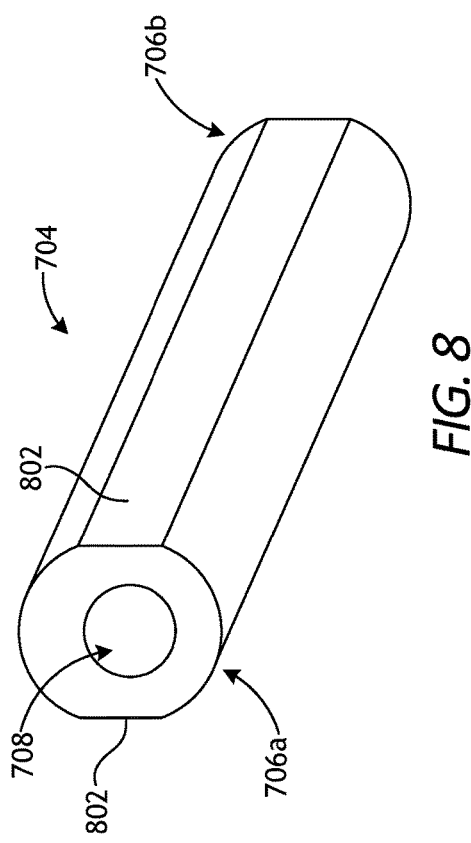
FIG. 8 is an isometric view of the longitudinal support structure of FIG. 7, according to one or more embodiments.

FIG. 8 is an isometric view of the longitudinal support structure 704, according to one or more embodiments. As illustrated, the longitudinal support structure 704 may comprise, for example, an elongate cylinder or tube that defines the channel 708 extending between the distal and proximal ends 706a,b. The longitudinal support structure 704 be made of any rigid or semi rigid materials including, but not limited to, a metal (e.g., tungsten, stainless steel, etc.), a polymer, a composite material, or any combination thereof.

In some embodiments, the longitudinal support structure 704 may exhibit a substantially circular cross-section. In at least one embodiment, however, the longitudinal support structure 704 may provide or otherwise define one or more planar sides or surfaces 802 that extend at least partially between the distal and proximal ends 706a,b on the exterior of the longitudinal support structure 704. In such embodiments, the sliding aperture 716 (FIG. 7) defined through the sliding element 714 (FIG. 7) may (or may not) exhibit a corresponding cross-sectional shape capable of mating with the planar surfaces 802. While two planar surfaces 802 are shown in FIG. 8, more or less than two may be employed. Moreover, while the planar surfaces 802 are depicted on angularly opposite sides of the longitudinal support structure 704, the planar surfaces 802 may alternatively be non-equidistantly separated from each other, without departing from the scope of the disclosure.

The planar surfaces 802 may prove advantageous helping support the sliding element 714 (FIG. 7) during longitudinal translation. Moreover, the planar surfaces 802 may also be dimensioned at a moment of inertia so that the longitudinal support structure 704 does not bend in the direction of the load, which would be generally parallel to the planar surfaces 802 in a pitch-like direction of the end effector 204 (FIG. 7). More specifically, the planar surfaces 802 may be dimensioned such that the longitudinal support structure 704 exhibits an increased moment of inertia, and thus resistance to bending, in the direction that the load is applied from the pivot link 710.

Figure 9A:
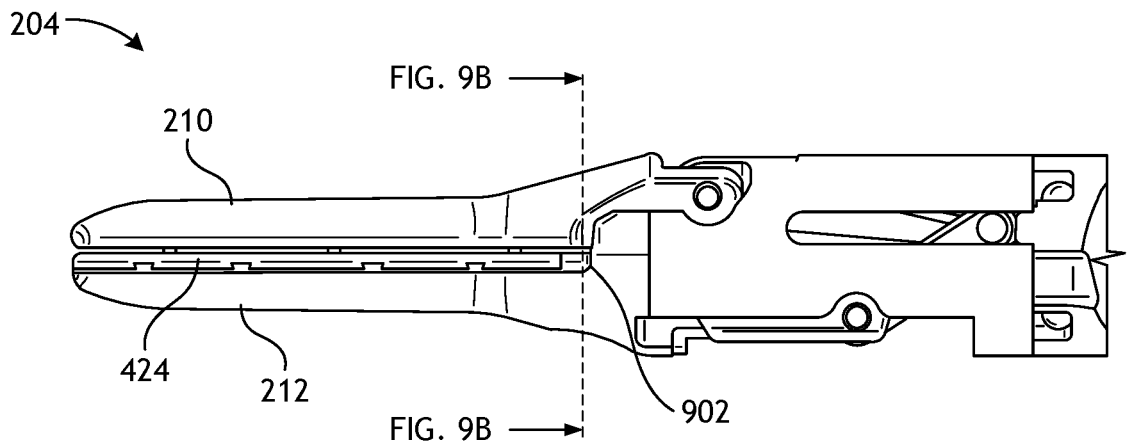
FIG. 9A is a side view of the end effector of FIG. 4 in the closed position.
Figure 9B:
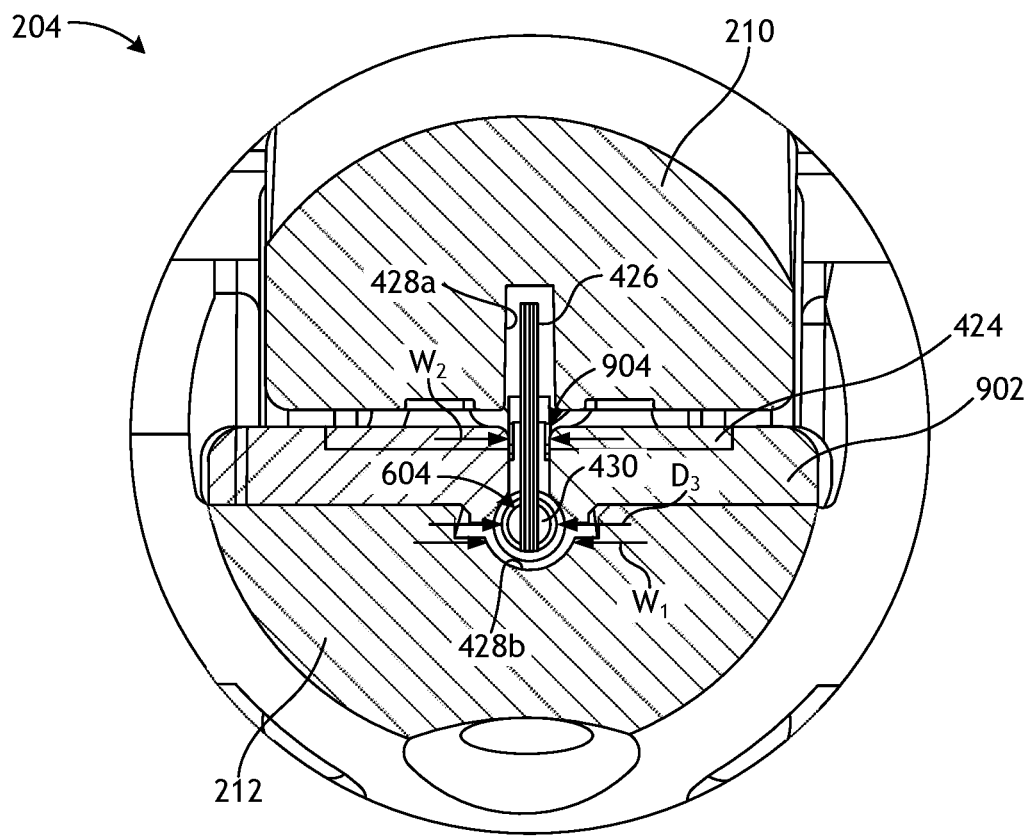
FIG. 9B is a cross-sectional end view of the end effector of FIG. 4 taken along the lines indicated in FIG. 9A.

FIG. 9A is a side view of the end effector 204 in the closed position, and FIG. 9B is a cross-sectional end view of the end effector 204 taken along the lines indicated in FIG. 9A. In the closed position, the upper jaw 210 extends substantially parallel to the lower jaw 212 and the electrode 424 may interpose at least a portion of the interface between the upper and lower jaws 210, 212. In some embodiments, as best seen in FIG. 9B, the electrode 424 may be mounted to the lower jaw 212 in conjunction with an insulator 902 that isolates the RF energy supplied to electrode 424 from the lower jaw 212 during operation. Isolation of the lower jaw 212 creates a single pathway for the electrical current to flow from the electrode 424 through the tissue and returning through the upper jaw 210. In at least one embodiment, the insulator 902 may comprise a non-conductive material overmolded onto the lower jaw 212. Suitable non-conductive materials include, but are not limited to, nylon, a polyphthalamide (e.g., GRIVORY® or THERMEC™), or a combination thereof.

Referring to FIG. 9B, corresponding guide tracks may be defined in the upper and lower jaws 210, 212, shown as a first or "upper" guide track 428a defined in the upper jaw 210 and a second or "lower" guide track 428b defined in the lower jaw 212. The upper and lower guide tracks 428a,b may be aligned such that the cutting element 426 is able to extend partially into each guide track 428a,b. As the cutting element 426 advances distally or is retracted proximally along the length of the jaws 210, 212, the guide tracks 428a,b cooperatively direct the travel path of the cutting element 426 and help prevent the cutting element 426 from twisting or otherwise falling (leaning) to one side or the other.

As briefly mentioned above, the retention feature 604 not only operatively couples the drive rod 430 to the cutting element 426, but may also be designed or otherwise configured to help the cutting element 426 follow the path defined by the lower guide track 428b. As illustrated, the lower guide track 428b may exhibit a width $W_1$, which is larger than the cross-sectional size or diameter $D_3$ of the retention feature 604. Consequently, the lower guide track 428b may be sized to accommodate (receive) the retention feature 604, which may guide the cutting element 426 as it moves back and forth within the lower guide track 428b during operation.

The lower guide track 428b may also be designed and otherwise configured to prevent the cutting element 426 from exiting the lower guide track 428b during distal or proximal movement. More particularly, an opening 904 to the lower guide track 428b may exhibit a width $W_2$, which may be smaller than the cross-sectional size or diameter $D_3$ of the retention feature 604. Consequently, the retention feature 604 may be retained (trapped) within the lower guide track 428b, which prevents the cutting element 426 from exiting the lower guide track 428b during operation. In some embodiments, as illustrated, the opening 904 may be defined by the electrode 424 or a combination of the electrode 424 and the insulator 902. In other embodiments, however, the opening 904 may be defined solely by the lower jaw 212, without departing from the scope of the disclosure.

In some embodiments, the width $W_2$ of the opening 904 may be slightly larger than the width of the cutting element 426. This may prove advantageous in reducing the likelihood of tissue ingress into the lower guide track 428b or tissue sticking during operation. The width of the upper guide track 428a may also be minimized or otherwise slightly larger than the width of the cutting element 426. This may help maintain the cutting element 426 upright during operation and also mitigate tissue ingress into the upper guide track 428a during operation.

Figure 10A:
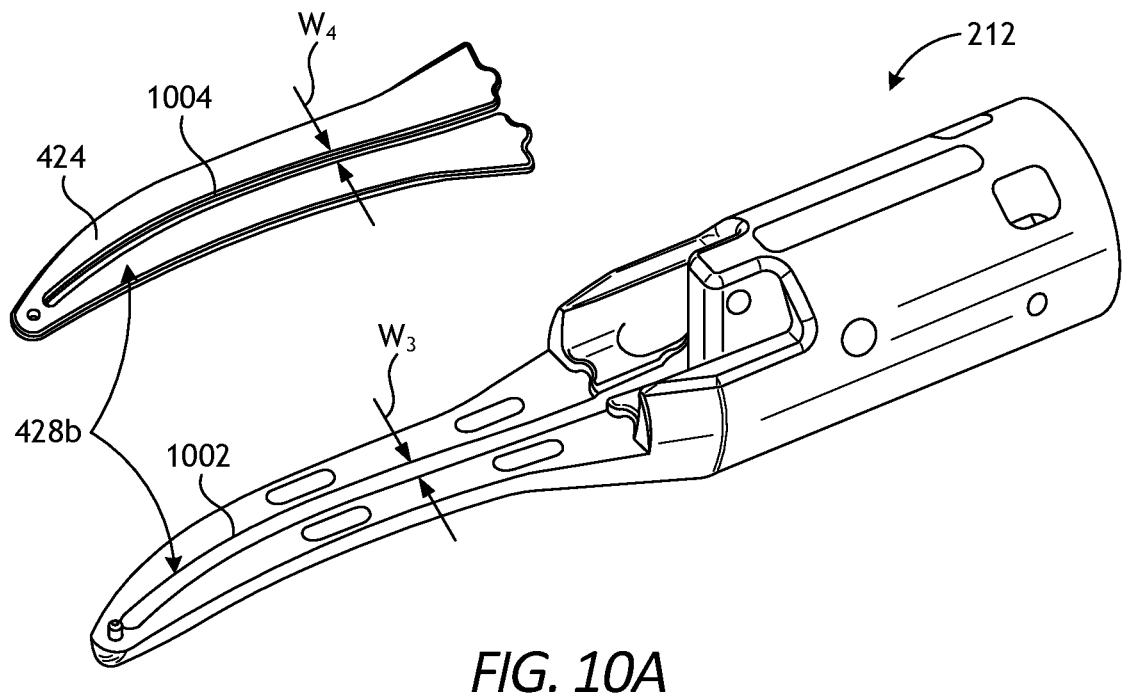
FIG. 10A is an exploded isometric view of an example of the lower jaw, according to one or more embodiments.

FIG. 10A is an exploded isometric view of one example of the lower jaw 212, according to one or more embodiments. As illustrated, the lower jaw 212 defines a jaw slot 1002 and the electrode 424 defines an electrode slot 1004. When the electrode 424 is properly mounted to the lower jaw 212, the jaw slot 1002 and the electrode slot 1004 align to cooperatively define the lower guide track 428b. The jaw slot 1002 exhibits a width $W_3$ and the electrode slot 1004 exhibits a width $W_4$ that is smaller than the width $W_3$ of the jaw slot 1002. In at least one embodiment, the electrode slot 1004 may be the same as or otherwise define the opening 904 (FIG. 9B) to the lower guide track 428b.

Figure 10B:
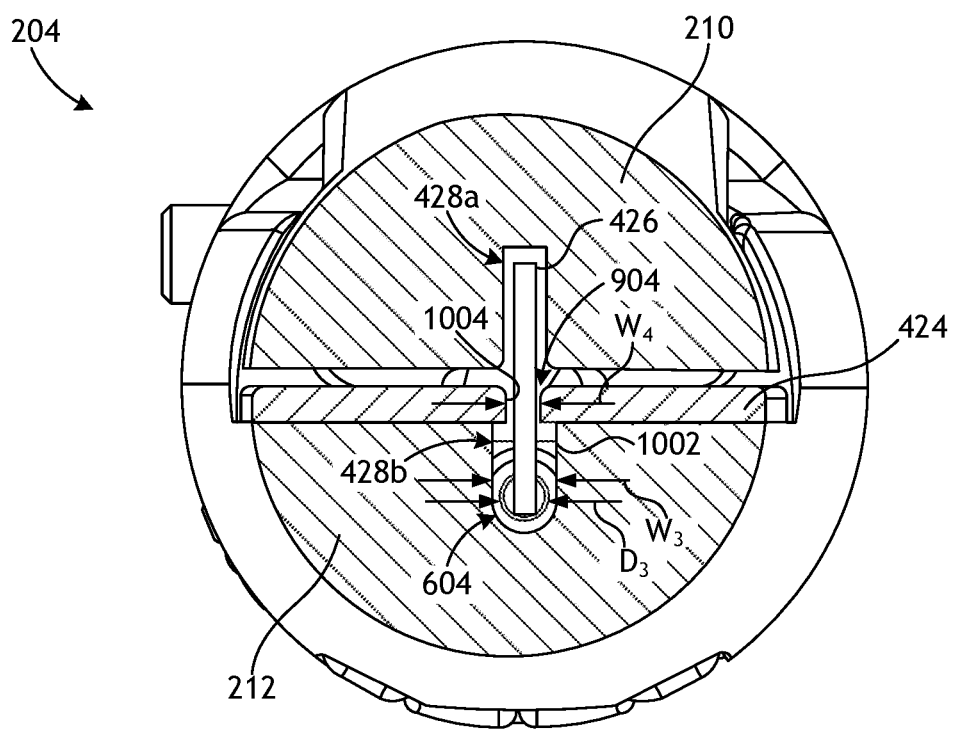
FIG. 10B is a cross-sectional end view of an alternative embodiment of the end effector of FIG. 4 that incorporates the lower jaw of FIG. 10A.

FIG. 10B is a cross-sectional end view of an alternative embodiment of the end effector 204 that incorporates the lower jaw 212 of FIG. 10A. As illustrated, the jaws 210, 212 are in the closed position and the electrode 424 may interpose at least a portion of the interface between the upper and lower jaws 210, 212. The upper and lower guide tracks 428a,b are aligned such that the cutting element 426 is able to extend partially into each guide track 428a,b.

In the illustrated embodiment, the width $W_3$ of the jaw slot 1002 is larger than the cross-sectional size or diameter $D_3$ of the retention feature 604. Consequently, the lower guide track 428b may be sized to accommodate (receive) the retention feature 604, which may guide the cutting element 426 as it moves back and forth within the lower guide track 428b during operation. Moreover, the electrode slot 1004 may provide or otherwise define the opening 904 to the lower guide track 428b. The width $W_4$ of the electrode slot 1004 may be smaller than the width $W_3$ of the cross-sectional size or diameter $D_3$ of the retention feature 604. Consequently, the retention feature 604 may be retained (trapped) within the lower guide track 428b, which prevents the cutting element 426 from exiting the lower guide track 428b during operation.

Figure 11A:
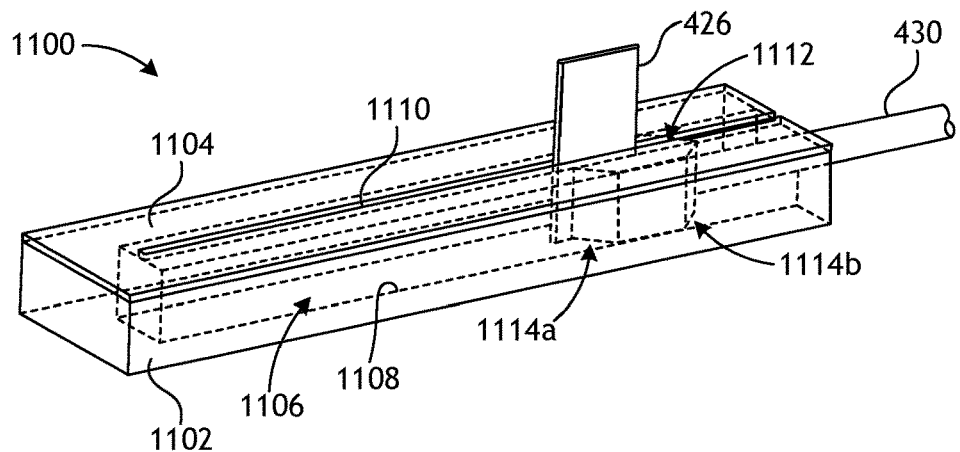
FIG. 11A is an isometric schematic view of an example lower jaw assembly, according to one or more embodiments.

FIG. 11A is an isometric schematic view of an example lower jaw assembly 1100, according to one or more embodiments. As illustrated, the lower jaw assembly 1100 may include a lower jaw 1102 shown in phantom (transparent), which may be similar in some respects to the lower jaw 212 of FIGS. 4, 9A-9B, and 10A-10B. An electrode 1104 may be mounted to the lower jaw 1102 and a lower guide track 1106 may be cooperatively provided or otherwise defined by the lower jaw 1102 and the electrode 1104. More particularly, the lower jaw 212 defines a jaw slot 1108 and the electrode 1104 defines an electrode slot 1110. When the electrode 1104 is properly mounted to the lower jaw 1102, the jaw and electrode slots 1108, 1110 align to cooperatively define the lower guide track 1106.

The cutting element 426 may be attached to the distal end of the drive rod 430 at a retention feature 1112 similar in some respects to the retention feature 604 of FIGS. 6A-6B. The retention feature 1112 may be designed to help the cutting element 426 follow the path defined by the lower guide track 1106, and may also prevent the cutting element 426 from exiting or disengaging the lower guide track 1106. In the illustrated embodiment, the retention feature 1112 comprises a support block that operatively couples the cutting element 426 to the drive rod 430 (FIG. 11A). In some embodiments, the retention feature 1112 may be overmolded onto one or both of the cutting element 426 and the drive rod 430, but may alternatively form a two-piece clamshell structure. The retention feature 1112 may be made of a variety of materials including, but not limited to a metal, a polymer, a composite material, or any combination thereof. In at least one embodiment, the retention feature 1112 may be made of a lubricious material, such as silicone, nylon, or a material infused or coated with silicone or nylon. Being made of (or infused with) a lubricious material may improve slidability of the retention feature 1112 within the lower guide track 1106.

In the illustrated embodiment, the retention feature 1112 may include first or "lead" end 1114a and a second or "tail" end 1114b opposite the lead end 1114a. As illustrated the lead and tail ends 1114a,b may be contoured. As used herein, the term "contoured" refers to one or both of the lead and tail ends 1114a,b being angled, chamfered, rounded, or otherwise non-perpendicular to the sidewalls of the lower guide track 1106. This may prove advantageous in helping to reduce friction and contact as the cutting element 426 is transitioned distally and proximally within the lower guide track 1106.

Figure 11B:
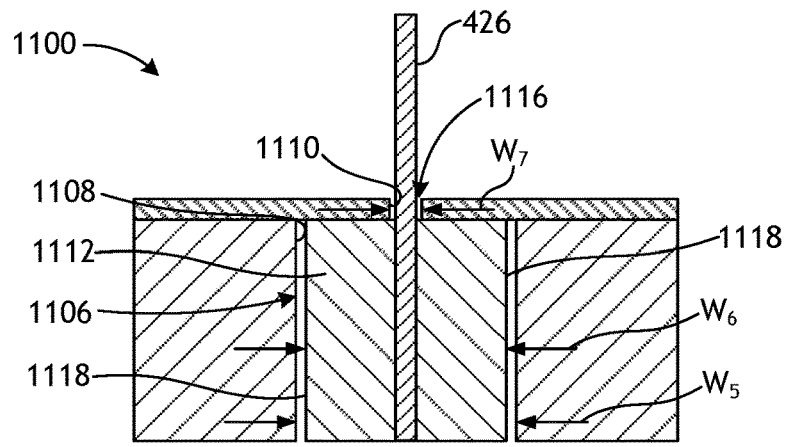
FIG. 11B is a cross-sectional end view of the jaw assembly of FIG. 11A taken through the retention feature of FIG. 11A.

FIG. 11B is a cross-sectional end view of the jaw assembly 1100 taken vertically through the retention feature 1112. As illustrated, the jaw slot 1108 provides a width $W_5$ that is larger than a cross-sectional size or width $W_6$ of the retention feature 1112. Consequently, the lower guide track 1106 may be sized to accommodate (receive) the retention feature 1112, which may guide the cutting element 426 as it moves within the lower guide track 1106 during operation.

The electrode slot 1110 of the electrode 1104 may provide or otherwise define an opening 1116 to the lower guide track 1106 through which the cutting element 426 extends. The electrode slot 1110 provides a width $W_7$ that may be smaller than the cross-sectional size or width $W_6$ of the retention feature 1112. Consequently, the retention feature 1112 may be retained (trapped) within the lower guide track 1106, which prevents the cutting element 426 from exiting the lower guide track 1106 during operation.

As illustrated, the retention feature 1112 may provide or otherwise define opposing sides 1118 that help align the retention feature 1112 within the lower guide track 1106. The sides 1118 may extend substantially parallel to the inner opposing walls of the lower guide track 1106. As the cutting element 426 is transitioned distally and proximally within the lower guide track 1106, the sides 1118 may help maintain the cutting element 426 erect and otherwise prevent the cutting element 426 from tipping over and prevent twisting of the retention feature 1112. This may prove advantageous in ensuring that the cutting element 426 will properly align with the upper guide track 428a (FIGS. 9B and 10B) of the upper jaw 212 (FIGS. 9B and 10B), which would otherwise interfere with the upper jaw 212 and prevent full closure or required clamp force.

Figure 11C:
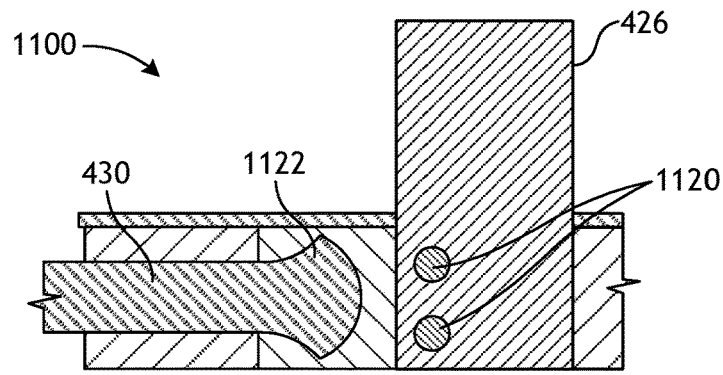
FIG. 11C is a cross-sectional side view of the of the jaw assembly of FIG. 11A taken through the retention feature of FIG. 11A.

FIG. 11C is a cross-sectional side view of the of the jaw assembly 1100 taken longitudinally through the retention feature 1112 of FIG. 11A. As illustrated, the retention feature 1112 operatively couples the cutting element 426 to the drive rod 430. In the illustrated embodiment, various features may be provided on the cutting element 426 and/or the drive rod 430 to help increase the retention forces of the retention feature 1112. In some embodiments, for example, one or more holes 1120 may be defined in the cutting element 426 at or near its base to help the retention feature 1112 adhere to the cutting element 426. In embodiments where the retention feature 1112 is overmolded onto the cutting element 426, the holes 1120 may allow the material of the retention feature 1112 to flow therethrough, which results in a more robust engagement between the cutting element 426 and the retention feature 1112. Moreover, in some embodiments, the distal end 1122 of the drive rod 430 may be flared or "coined". In embodiments where the retention feature 1112 is overmolded onto the distal end 1122 of the drive rod 430, the flared feature may enhance the retention forces between the drive rod 430 and the retention feature 1112. As will be appreciated, the holes 1120 and the flared distal end 1122 are not required, but may prove advantageous in ensuring a more robust connective force to allow for better retention during the retraction of the cutting element 426.

Embodiments disclosed herein include:

A. An end effector that includes first and second jaws movable between open and closed positions, a guide track defined in the second jaw, a cutting element extendable into the guide track and longitudinally movable within the guide track, and a retention feature positioned within the guide track and operatively coupling the cutting element to a drive rod, wherein the drive rod is actuatable to move the cutting element within the guide track, and wherein the retention feature is larger than a width of an opening to the guide track such that the retention feature is retained within the guide track as the cutting element moves.

B. A surgical tool that includes a drive housing, an elongate shaft that extends from the drive housing, and an end effector arranged at a distal end of the elongate shaft and including first and second jaws movable between open and closed positions, a guide track defined in the second jaw, a cutting element extendable into the guide track and longitudinally movable within the guide track, and a retention feature positioned within the guide track and operatively coupling the cutting element to a drive rod extending from the drive housing, wherein the drive rod is actuatable to move the cutting element within the guide track, and wherein the retention feature is larger than a width of an opening to the guide track such that the retention feature is retained within the guide track as the cutting element moves.

C. A method of operating a surgical tool that includes positioning the surgical tool adjacent a patient for operation, the surgical tool including a drive housing, an elongate shaft that extends from the drive housing, and an end effector arranged at a distal end of the elongate shaft, the end effector including first and second jaws movable between open and closed positions, a guide track defined in the second jaw, a cutting element extending into the guide track, and a retention feature that operatively couples the cutting element to a drive rod, wherein the retention feature is larger than a width of an opening to the guide track. The method further including actuating the first and second jaws to close and grasp onto tissue, actuating the drive rod and thereby longitudinally moving the cutting element within the guide track to transect the tissue, and retaining the retention feature and the cutting element within the guide track as the cutting element moves.

Each of embodiments A, B, and C may have one or more of the following additional elements in any combination: Element 1: further comprising an electrode coupled to the second jaw, wherein the opening is defined by the electrode. Element 2: further comprising an insulator mounted to the second jaw, wherein the electrode is mounted to the insulator and the opening is defined by a combination of the electrode and the insulator. Element 3: wherein the guide track is a lower guide track and the end effector further comprises an upper guide track defined in the first jaw and alignable with the lower guide track when the first and second jaws are in the closed position, and wherein the cutting element extends partially into the upper guide track. Element 4: wherein retention feature is selected from the group consisting of a welded interface, an adhesive attachment, an interference or shrink fit, an overmold, one or more mechanical fasteners, and any combination thereof. Element 5: wherein the retention feature comprises a support block having at least one side that extends parallel to an opposing sidewall of the guide track to help maintain the cutting element erect and prevent the retention feature from twisting. Element 6: wherein the retention feature provides a first end and a second end opposite the first end, and wherein at least one of the first and second ends is contoured. Element 7: wherein the retention feature is made of or infused with a lubricious material. Element 8: further comprising a longitudinal support structure defining a longitudinal channel that receives the drive rod, wherein the drive rod is movable within the channel and the longitudinal support structure prevents buckling of the drive rod. Element 9: wherein the longitudinal support structure provides a hard stop that stops proximal movement of the cutting element.

Element 10: further comprising an electrode coupled to the second jaw, wherein the opening is defined by the electrode. Element 11: further comprising an insulator mounted to the second jaw, wherein the electrode is mounted to the insulator and the opening is defined by a combination of the electrode and the insulator. Element 12: wherein the guide track is a lower guide track and the end effector further comprises an upper guide track defined in the first jaw and alignable with the lower guide track when the first and second jaws are in the closed position, and wherein the cutting element extends partially into the upper guide track. Element 13: wherein the end effector further includes a longitudinal support structure defining a longitudinal channel that receives the drive rod, and wherein the drive rod is movable within the channel and the longitudinal support structure prevents buckling of the drive rod. Element 14: further comprising an articulable wrist that interposes the end effector and the elongate shaft, wherein the drive rod extends through the articulable wrist.

Element 15: wherein the end effector further includes an electrode coupled to the second jaw and the opening is defined by the electrode, the method further comprising providing electrical energy to the electrode with an electrical conductor extending from the drive housing, cauterizing or coagulating the grasped tissue, and transecting the grasped tissue after cauterizing or coagulating the grasped tissue. Element 16: wherein the end effector further includes a longitudinal support structure defining a longitudinal channel that receives the drive rod, and wherein actuating the drive rod further comprises moving the drive rod within the channel, and preventing buckling of the drive rod with the longitudinal support structure. Element 17: wherein the guide track is a lower guide track and the end effector further comprises an upper guide track defined in the first jaw and alignable with the lower guide track when the first and second jaws are in the closed position, the method further comprising moving the cutting element within the upper and lower guide tracks to transect the tissue.

By way of non-limiting example, exemplary combinations applicable to A, B, and C include: Element 1 with Element 2; Element 5 with Element 6; Element 8 with Element 9; and Element 10 with Element 11.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector, comprising:
   first and second jaws movable between open and closed positions;
   a guide track defined in the second jaw;
   a cutting element extendable into the guide track and longitudinally movable within the guide track;
   a retention feature operatively coupling the cutting element to a drive rod actuatable to move the cutting element and the retention feature within the guide track, wherein the retention feature is larger than a width of an opening to the guide track such that the retention feature is retained within the guide track as the cutting element moves;
   a longitudinal support structure extending between the first and second jaws and an articulable wrist, the longitudinal support structure defining a longitudinal channel extending between distal and proximal ends of the longitudinal support structure to receive and prevent buckling of the drive rod; and
   a hard stop provided at the distal end of the longitudinal support structure to prevent the cutting element and the retention feature from entering the longitudinal channel.

2. The end effector of claim 1, further comprising an electrode coupled to the second jaw, wherein the opening is defined by the electrode.

3. The end effector of claim 2, further comprising an insulator mounted to the second jaw, wherein the electrode is mounted to the insulator and the opening is defined by a combination of the electrode and the insulator.

4. The end effector of claim 1, wherein the guide track is a lower guide track and the end effector further comprises an upper guide track defined in the first jaw and alignable with the lower guide track when the first and second jaws are in the closed position, and wherein the cutting element extends partially into the upper guide track.

5. The end effector of claim 1, wherein the retention feature is selected from the group consisting of a welded interface, an adhesive attachment, an interference or shrink fit, an overmold, one or more mechanical fasteners, and any combination thereof.

6. The end effector of claim 1, wherein the retention feature comprises a support block having at least one side that extends parallel to an opposing sidewall of the guide track to help maintain the cutting element erect and prevent the retention feature from twisting.

7. The end effector of claim 6, wherein the retention feature provides a first end and a second end opposite the first end, and wherein at least one of the first and second ends is contoured.

8. The end effector of claim 1, wherein the retention feature is made of or infused with a lubricious material.

9. The end effector of claim 1, wherein a distal end of the longitudinal support structure is supported by the second jaw at all times as the first and second jaws move between the open and closed positions.

10. The end effector of claim 1, wherein the hard stop comprises a longitudinal rib defined on the longitudinal support structure and aligned to engage the cutting element when the drive rod moves the cutting element proximally.

11. The end effector of claim 1, wherein the hard stop comprises a distal opening defined on the longitudinal support structure, the distal opening exhibiting a diameter smaller than a diameter of the retention feature.

12. A surgical tool, comprising:
    a drive housing;
    an elongate shaft that extends from the drive housing;
    an end effector arranged at a distal end of the elongate shaft and including:
      first and second jaws movable between open and closed positions;
      a guide track defined in the second jaw;
      a cutting element extendable into the guide track and longitudinally movable within the guide track; and
      a retention feature operatively coupling the cutting element to a drive rod extending from the drive housing;

an articulable wrist interposing the end effector and the elongate shaft; and a longitudinal support structure extending between the end effector and the articulable wrist, the longitudinal support structure defining a longitudinal channel extending between distal and proximal ends of the longitudinal support structure to receive and prevent buckling of the drive rod, wherein a hard stop is provided at the distal end of the longitudinal support structure prevents the cutting element and the retention feature from entering the longitudinal channel, and wherein the drive rod is actuatable to move the cutting element within the guide track, and the retention feature is larger than a width of an opening to the guide track such that the retention feature is retained within the guide track as the cutting element moves.

13. The surgical tool of claim 12, further comprising an electrode coupled to the second jaw, wherein the opening is defined by the electrode.

14. The surgical tool of claim 13, further comprising an insulator mounted to the second jaw, wherein the electrode is mounted to the insulator and the opening is defined by a combination of the electrode and the insulator.

15. The surgical tool of claim 12, wherein the guide track is a lower guide track and the end effector further comprises an upper guide track defined in the first jaw and alignable with the lower guide track when the first and second jaws are in the closed position, and wherein the cutting element extends partially into the upper guide track.

16. A method of operating a surgical tool, comprising:
positioning the surgical tool adjacent a patient for operation, the surgical tool including a drive housing, an elongate shaft extending from the drive housing, an end effector arranged at a distal end of the elongate shaft, and an articulable wrist interposing the end effector and the elongate shaft, the end effector including:
first and second jaws movable between open and closed positions;
a guide track defined in the second jaw;
a cutting element extending into the guide track; and
a retention feature that operatively couples the cutting element to a drive rod and is larger than a width of an opening to the guide track;
actuating the first and second jaws to close and grasp onto tissue;
actuating the drive rod and thereby longitudinally moving the cutting element within the guide track to transect the tissue;
preventing buckling of the drive rod with a longitudinal support structure extending between the end effector and the articulable wrist, the longitudinal support structure defining a longitudinal channel extending between distal and proximal ends of the longitudinal support structure to receive the drive rod;
retaining the retention feature and the cutting element within the guide track as the cutting element moves; and
retracting the cutting element and preventing the cutting element and the retention feature from entering the longitudinal channel with a hard stop provided at the distal end of the longitudinal support structure.

17. The method of claim 16, wherein the end effector further includes an electrode coupled to the second jaw and the opening is defined by the electrode, the method further comprising:
providing electrical energy to the electrode with an electrical conductor extending from the drive housing;
cauterizing or coagulating the grasped tissue; and
transecting the grasped tissue after cauterizing or coagulating the grasped tissue.

18. The method of claim 16, wherein the guide track is a lower guide track and the end effector further comprises an upper guide track defined in the first jaw and alignable with the lower guide track when the first and second jaws are in the closed position, the method further comprising moving the cutting element within the upper and lower guide tracks to transect the tissue.

* * * * *